United States Patent [19]

Stults

[11] Patent Number: 4,946,985

[45] Date of Patent: Aug. 7, 1990

[54] CATALYZED PROCESS FOR THE PREPARATION OF OXYDIPHTHALIC ANHYDRIDES

[75] Inventor: Jeffrey S. Stults, Grand Island, N.Y.

[73] Assignee: Occidental Chemical Corporation, Niagara Falls, N.Y.

[21] Appl. No.: 284,219

[22] Filed: Dec. 14, 1988

[51] Int. Cl.$^5$ .......................................... C07D 307/89
[52] U.S. Cl. ................................................... 549/241
[58] Field of Search ........................................ 549/241

[56] References Cited

U.S. PATENT DOCUMENTS

| | | | |
|---|---|---|---|
| 4,288,386 | 9/1981 | Soula et al. | 549/453 |
| 4,697,023 | 9/1987 | Schwartz et al. | 549/241 |
| 4,808,731 | 2/1989 | Berdahl et al. | 549/241 |

OTHER PUBLICATIONS

Gowan & Wheeler *Name Index of Organic Reactions,* 1960, p. 244.
Morrison & Boyd *Organic Chemistry* 3rd ed., 1974, pp. 790–791.

*Primary Examiner*—Richard L. Raymond
*Assistant Examiner*—Raymond Covington
*Attorney, Agent, or Firm*—James F. Tao; Arthur S. Cookfair

[57] ABSTRACT

Oxydiphthalic anhydrides are prepared by reacting a halophthalic anhydride with water and an alkali metal compound such as KF, CsF, or $K_2CO_3$ in the presence of a copper catalyst.

22 Claims, No Drawings

CATALYZED PROCESS FOR THE PREPARATION OF OXYDIPHTHALIC ANHYDRIDES

BACKGROUND OF THE INVENTION

This invention relates to a method for the preparation of oxydiphthalic anhydrides. The products are useful chemical intermediates for the further preparation of various compounds such as the corresponding dicarboxylic acids and the various derivatives thereof, including for example, the salts, esters, acyl halides, amides, imides, and the like. The oxydiphthalic anhydrides are particularly useful as monomers in the preparation of polyimides, for example by polycondensation with a suitable diamine, such as ethylenediamine or phenylenediamine.

Various methods for the preparation of oxydiphthalic anhydrides have been described in the chemical literature. One such method, shown to be useful in the preparation of oxydiphthalic acids and anhydrides, involves the oxidation of tetramethyl diphenyl ethers. See Kolesnikov, G. S. et al *Vysokomol. Soyed,* A9, 612-18 (1967); Marvel, C. S. et al, *J. Am. Chem. Soc.,* 80, 1197 (1958); and Latrova, Z. N. et al, *Volokna Sin. Polim.,* 15-24 (1970).

Three Japanese patents to Mitsui describe preparations based on reactions of substituted phthalic anhydrides. Japanese Patent Document No. 80/136, 246 (Chem. Abst. 95:42680) teaches the coupling of 4-nitrophthalic anhydride in the presence of sodium nitrite to form oxydiphthalic anhydride. In Japanese Patent Document No. 80/122,738 (Chem. Abst. 94:83799) Mitsui disclose the reaction of 4-halophthalic acid or anhydride with a base to yield oxydiphthalic anhydride. In Japanese Patent Document No. 80/127,343 (Chem. Abst. 94:191942) the reaction of 4-halophthalic anhydride, Na$_2$CO$_3$ and NaNO$_2$ in dimethyl sulfoxide to form 4,4'-dihydroxydiphthalylic anhydride is described.

German Pat. No. 2,416,594 (1975) discloses the coupling of 3-nitrophthalic anhydride in the presence of metal nitrites, such as sodium nitrite to form oxydiphthalic anhydride.

Markezich, R. L. and Zamek, O. S., *J. Org. Chem.,* 42, 3431 (1977) describe reaction of 4-nitrophthalimide with potassium fluoride in dimethylsulfoxide to form the corresponding oxydiphthalimide which may be converted by hydrolysis to form the acid and ring closure to form the dianhydride.

U.S. Pat. No. 4,697,023 to Schwartz et al, discloses the preparation of oxydiphthalic anhydrides by reaction of a halophthalic anhydride with water and an alkali metal compound, such as KF, CsF, or K$_2$CO$_3$.

SUMMARY OF THE INVENTION

In has now been found that diphthalic ether dianhydrides of the formula

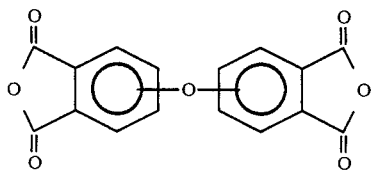

can be prepared by reacting a halophthalic anhydride of the formula

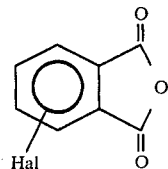

where Hal is F or Br with water and an alkali metal compound selected from the group consisting of KF, CsF, and K$_2$CO$_3$ in the presence of a copper catalyst.

In the reaction the halogen atom site on the halophthalic anhydride reactant becomes the site for the formation of the ether bridge. Thus, when the reactant is a 4-halophthalic anhydride such as

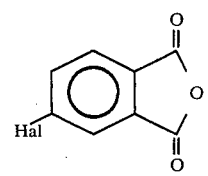

where Hal is F or Br, the oxydiphthalic product will be 4,4'-oxydiphthalic anhydride characterized by the formula

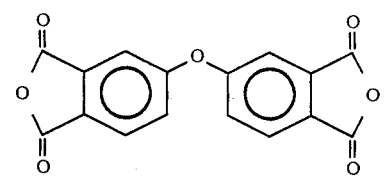

When the reactant is 3-halophthalic anhydride, the oxydiphthalic product will be 3,3'-oxydiphthalic anhydride, characterized by the formula

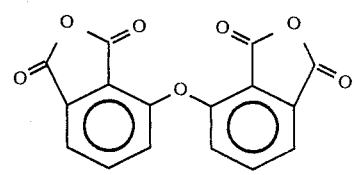

Alternatively, a mixture of the 3-halo- and 4-halophthalic anhydrides may be employed as the starting reactant, to form, in addition to the 4,4'- and 3,3'-oxydiphthalic anhydride isomers, and a 3,4'-oxydiphthalic anhydride of the formula

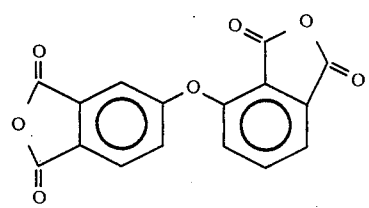

The halogen substituent on the starting halophthalic anhydride reactant may be F or Br. The preferred compound, based on economic as well as chemical considerations is 4-fluorophthalic anhydride. The alkali metal compound may be potassium fluoride, cesium fluoride or potassium carbonate. Based on economic considerations, the preferred alkali metal compound is potassium carbonate. The proportions of reactants may vary considerably, however, it is recommended that the alkali metal compound be employed in sufficient proportions to provide at least about one equivalent of potassium (or cesium) per mole of halophthalic anhydride. Preferably the alkali metal compound is employed in substantial excess, for example, up to about 50 percent excess of the aforesaid equivalent proportions.

Suitable copper catalysts that may be employed in the process of this invention include elemental copper, cuprous oxide, cupric oxide, copper chromite, bis[copper (I) trifluoromethanesulfonate], benzene complex (i.e., copper (1) triflate), copper (II) trifluoromethanesulfonate (i.e., copper (II) triflate), copper (I) bromide (most conveniently as a stabilized complex, such as copper (I) bromide-dimethylsulfide complex), copper sulfate, cupric tetrafluoroborate and cuprous benzoate.

Water may be a limiting reactant and ideally, for maximum efficiency, is preferably present in a molar proportion of $H_2O$ halophthalic anhydride of about 0.5. The water may be added to the initial reaction mixture or, alternatively, may be generated in-situ. For example, when potassium carbonate is employed in the reaction mixtures, a trace amount of water may be present in the initial reaction mixture and additional water generated in-situ as the reaction proceeds.

The process of the invention is preferably carried out at atmospheric pressure, however, sub-atmospheric, or super-atmospheric pressure, for example, under autogenous conditions, may be employed if desired. The process is preferably carried out in the presence of a solvent. Suitable solvents include both apolar and polar solvents, the preferred solvents being polar, aprotic solvents, such as N-methyl-pyrrolidone, dimethyl formamide, dimethyl acetamide, triglyme, sulfolane, or the like. The most preferred solvent is sulfolane.

The temperature at which the process is carried out may vary considerably, but will generally be within the range of about 110° to about 210° Celsius. Higher or lower temperatures may be employed but are generally less efficient. At higher temperatures the halophthalic anhydride reactant may undergo decarboxylation. The optimum temperature may vary somewhat depending on the choice of solvent and, more importantly, on the particular halophthalic anhydride and copper catalyst employed. For most of the copper catalysts that may be employed, the preferred temperature range is about 130° to 200° Celsius.

The following examples are provided to further illustrate this invention and the manner in which it may be carried out. It will be understood, however, that the specific details given in the examples have been chosen for purposes of illustration only and are not to be construed as limiting the invention. In the examples, unless otherwise indicated, all parts and percentages are by weight and all temperatures are in degrees Celsius.

EXAMPLE 1

A mixture of 4-fluorophthalic anhydride (16.69 g), potassium fluoride (6.4 g), cuprous oxide (1.7 g), and dimethyl formamide (16.6 ml) was heated to 130° C. and 0.9 g of water was added. The reaction mixture was heated to 170° C. and maintained thereat, with stirring for 1.5 hours.

Analysis by gas chromatography with an internal standard, indicated 85% oxydiphthalic anhydride.

When the example was repeated except that no catalyst was present, no oxydiphthalic was detected in the reaction product after 1.5 hours. (However, continued heating resulted in oxydiphthalic anhydride formation.)

EXAMPLE 2

4-Fluorophthalic anhydride (27 g), cuprous oxide (1.35 g), and dimethyl formamide (60 ml), containing a trace amount of water, were mixed and heated to 130° C. Potassium carbonate (11.3 g) was added. The reaction mixture was heated to 149°–152° C. and maintained thereat, with stirring, for about 10 hours. The reaction mixture was filtered hot and the dimethyl formamide was removed under reduced pressure on a rotary evaporator. The remaining solid was slurried in 1,2,4-trichlorobenzene, heated to reflux, filtered, and cooled to room temperature to yield 16.6 g of oxydiphthalic anhydride.

EXAMPLE 3

A mixture of 4-fluorophthalic anhydride (12.45 g), and cuprous oxide (1.2 g) in sulfolane (35 ml), containing a trace amount of water was heated to 130° C. and potassium carbonate (6.9 g) was added. The mixture was heated to 175° C. and maintained thereat, with stirring for about 3 hours. The reaction mixture was analyzed by gas chromatography using an internal standard with the results as shown in Table 1 below.

EXAMPLE 4

The procedure of Example 3 was repeated except that in place of the cuprous oxide there was substituted an equal amount of copper sulfate and the reaction was continued for 2 hours with the results as shown in Table 1 below.

EXAMPLE 5

The procedure of Example 1 was repeated except that no copper catalyst was added and the reaction was continued for 4.5 hours with the results as shown in Table 1 below.

TABLE 1

| Reactant (g) | Example Numbers | | |
|---|---|---|---|
| | 3 | 4 | 5 |
| 4-Fluorophthalic anhydride | 12.45 | 12.45 | 12.45 |
| Sulfolane (ml) | 35.0 | 35.0 | 35.0 |
| $K_2CO_3$ | 6.9 | 6.9 | 6.9 |
| $Cu_2O$ | 1.2 | — | — |
| $CuSO_4$ | — | 1.2 | — |
| Reaction Temperature (°C.) | 175 | 175 | 175 |
| Reaction Time (hours) | 3.0 | 2.0 | 4.5 |
| Oxydiphthalic Anhydride (G.C. Area Percent) | 71 | 68 | 3.0 |

EXAMPLE 6

A mixture of 4-bromophthalic anhydride (10 g), and cuprous oxide (0.1 g) in sulfolane (20 ml), containing a trace amount of water, was heated to 187° C. Potassium carbonate (3.3 g) was added and the mixture was maintained with stirring, at a temperature range of 185°–200° C. for a period of 0.5 hours. The reaction mixture was analyzed by gas chromatography, using an internal standard, with the results as shown in Table 2, below.

EXAMPLE 7

The procedure of Example 6 was repeated except that in place of the cuprous oxide catalyst there was substituted an equal amount of cuprous benzoate and the reaction was carried out at 187°–200° C. for a period of 0.6 hours, with the results as shown in Table 2, below.

EXAMPLE 8

The procedure of Example 6 was repeated except that in place of the cuprous oxide catalyst there was substituted an equal amount of copper triflate (Cu-(OTF) and the reaction conditions were varied as shown in Table 2, below.

EXAMPLE 9

The procedure of Example 6 was repeated except that no copper catalyst was employed. Following the initial reaction period of 0.5 hours the reaction was continued at 200° C. for an additional 3.5 hours, with the results as shown in Table 2, below. (9a)

TABLE 2

| Reactant (g) | Example Numbers | | | | |
|---|---|---|---|---|---|
| | 6 | 7 | 8 | 9 | 9A |
| 4-Bromophthalic anhydride | 10.0 | 10.0 | 10.0 | 10.0 | 10.0 |
| Sulfolane (ml) | 20.0 | 20.0 | 20.0 | 20.0 | 20.0 |
| Potassium carbonate | 3.3 | 3.3 | 3.3 | 3.3 | 3.3 |
| Copper Catalyst: None | | | | — | — |
| Cuprous oxide | 0.1 | | | — | — |
| Cuprous benzoate | | 0.1 | | — | — |
| Copper triflate | | | 0.1 | | |
| Reaction temperature (° C.) | 185–200 | 187–200 | 200 | 185–200 | 200 |
| Reaction Time (Hours) | 0.5 | 0.6 | 2.5 | 0.5 | 4 |
| Oxydiphthalic anhydride (GC Area Percent) | 70 | 95 | 80 | 0 | 50 |

EXAMPLE 10

A mixture of 4-fluorophthalic anhydride (5.04 g), potassium carbonate (2.33 g), cuprous benzoate (0.25 g), and dimethyl formamide (30.0 ml), containing a trace amount of water, was heated to 134° C. and maintained thereat, with stirring for 1.3 hours. Analysis of the crude reaction product by gas chromatography indicated 55.5% oxydiphthalic anhydride.

When a similar reaction was attempted, except that no copper catalyst was present, no oxydiphthalic anhydride was detected.

EXAMPLE 11

A mixture of 4-fluorophthalic anhydride (33.2 g), potassium carbonate (13.8 g), cuprous oxide (1.6 g), and dimethyl formamide (66 ml), containing a trace amount of water, and was heated to 145°–149° C. and maintained in that temperature range, with stirring for eleven hours. Analysis of the crude reaction product by gas chromatography indicated 63.0% oxydiphthalic anhydride.

What is claimed is:

1. A process for the preparation of a diphthalic ether dianhydride of the formula

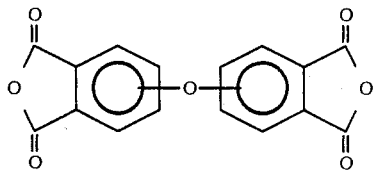

comprising reacting a halophthalic anhydride of the formula

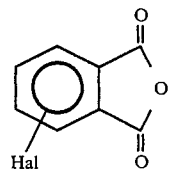

where Hal is F or Br, with water and an alkali metal compound selected from the group consisting of potassium fluoride, cesium fluoride, and potassium carbonate in the presence of a copper catalyst selected from the group consisting of elemental copper, cuprous oxide, cupric oxide, copper chromite, copper (I) triflate-benzene complex, copper (II) triflate, stabilized copper (I) bromide, copper sulfate, cupric tetrafluoroborate, and cuprous benzoate and mixtures thereof.

2. A process according to claim 1 wherein the halophthalic anhydride is characterized by the formula 3. A process according to claim 2, wherein the alkali metal compound is potassium carbonate.

4. A process according to claim 1, wherein the halophthalic anhydride is characterized by the formula 5. A process according to claim 4, wherein the alkali metal compound is potassium carbonate.

6. A process according to claim 1, wherein the alkali metal compound is potassium fluoride.

7. A process according to claim 1, carried out in a polar, aprotic solvent.

8. A process according to claim 7, wherein the solvent is selected from the group consisting of sulfolane and N,N-dimethyl formamide.

9. A process for the preparation of 4,4'-oxydiphthalic anhydride which comprises reacting 4-fluorophthalic anhydride with water and an alkali metal compound selected from the group consisting of potassium fluoride, cesium fluoride, and potassium carbonate in the presence of a copper catalyst selected from the group consisting of elemental copper, cuprous oxide, cupric oxide, copper chromite, copper (I) triflate-benzene complex, copper (II) triflate, stabilized copper (I) bromide, copper sulfate, cupric tetrafluoroborate, and cuprous benzoate and mixtures thereof.

10. A process according to claim 9, wherein the alkali metal compound is potassium carbonate.

11. A process according to claim 9, wherein the alkali metal compound is potassium fluoride.

12. A process according to claim 10, carried out in apolar, aprotic solvent.

13. A process according to claim 12 wherein the solvent is N,N-dimethylformamide.

14. A process according to claim 12 wherein the solvent is sulfolane.

15. A process according to claim 12, carried out at a temperature of about 130° to about 200° Celsius.

16. A process for the preparation of 4,4'-diphthalic ether dianhydride comprising reacting 4-bromophthalic anhydride with water and an alkali metal compound selected from the group consisting of KF, CsF, and $K_2CO_3$ in the presence of a copper catalyst selected from the group consisting of elemental copper, cuprous oxide, cupric oxide, copper chromite, copper (I) triflate-benzene complex, copper (II) triflate, copper (I) bromide-dimethylsulfide complex, copper sulfate, cupric tetrafluoroborate, and cuprous benzoate.

17. A process according to claim 16 wherein the alkali metal compound is potassium carbonate.

18. A process according to claim 16 wherein the alkali metal compound is potassium fluoride.

19. A process according to claim 17 carried out in a polar aprotic solvent.

20. A process according to claim 19 wherein the solvent is N,N-dimethylformamide.

21. A process according to claim 19 wherein the solvent is sulfolane.

22. A process according to claim 19 carried out at a temperature of about 180° to about 200° Celsius.

* * * * *